United States Patent [19]

Vinciguerra

[11] Patent Number: 5,609,645

[45] Date of Patent: Mar. 11, 1997

[54] KNEE REVISION PROSTHESIS WITH SHIMS

[75] Inventor: John D. Vinciguerra, Austin, Tex.

[73] Assignee: Intermedics, Inc., Angleton, Tex.

[21] Appl. No.: 589,570

[22] Filed: Jan. 22, 1996

Related U.S. Application Data

[63] Continuation of Ser. No. 331,049, Oct. 28, 1994.

[51] Int. Cl.$^6$ .................................................. A61F 2/38
[52] U.S. Cl. ................................................. 623/20; 623/18
[58] Field of Search ................................. 623/18, 20, 21

[56] References Cited

U.S. PATENT DOCUMENTS

| | | | |
|---|---|---|---|
| 4,731,086 | 3/1988 | Whiteside et al. | 623/20 |
| 4,936,847 | 6/1990 | Manginelli | 623/20 |
| 4,950,298 | 8/1990 | Gustilo et al. | 623/20 |
| 4,963,152 | 10/1990 | Hofmann et al. | 623/18 |
| 5,062,852 | 11/1991 | Dorr et al. | 623/20 |
| 5,071,438 | 12/1991 | Jones et al. | 623/20 |
| 5,116,375 | 5/1992 | Hofmann | 623/20 |
| 5,226,915 | 7/1993 | Bertin | 623/20 |
| 5,258,032 | 11/1993 | Bertin | 623/20 |
| 5,263,498 | 11/1993 | Caspari et al. | 623/20 |
| 5,405,398 | 4/1995 | Buford, III et al. | 623/20 |
| 5,411,505 | 5/1995 | Mumme | 606/88 |

FOREIGN PATENT DOCUMENTS 2223174  4/1990  United Kingdom ............... 623/20

Primary Examiner—John G. Weiss
Assistant Examiner—Bruce E. Snow
Attorney, Agent, or Firm—John R. Merkling

[57] ABSTRACT

A femoral knee prosthesis having a box internal geometry adjacent the femur which has four intersecting planes which extend from the medial side of the prosthesis to the lateral side. Shims of varying thickness can be added which retain the same internal box geometry. The internal geometry of the shims comprises three intersecting planes. Medial and lateral shims are provided. The internal geometry of the shims is translated slightly anteriorly as they increase in thickness. The shims may be added to either condyle independently, with different thickness on each side.

18 Claims, 5 Drawing Sheets

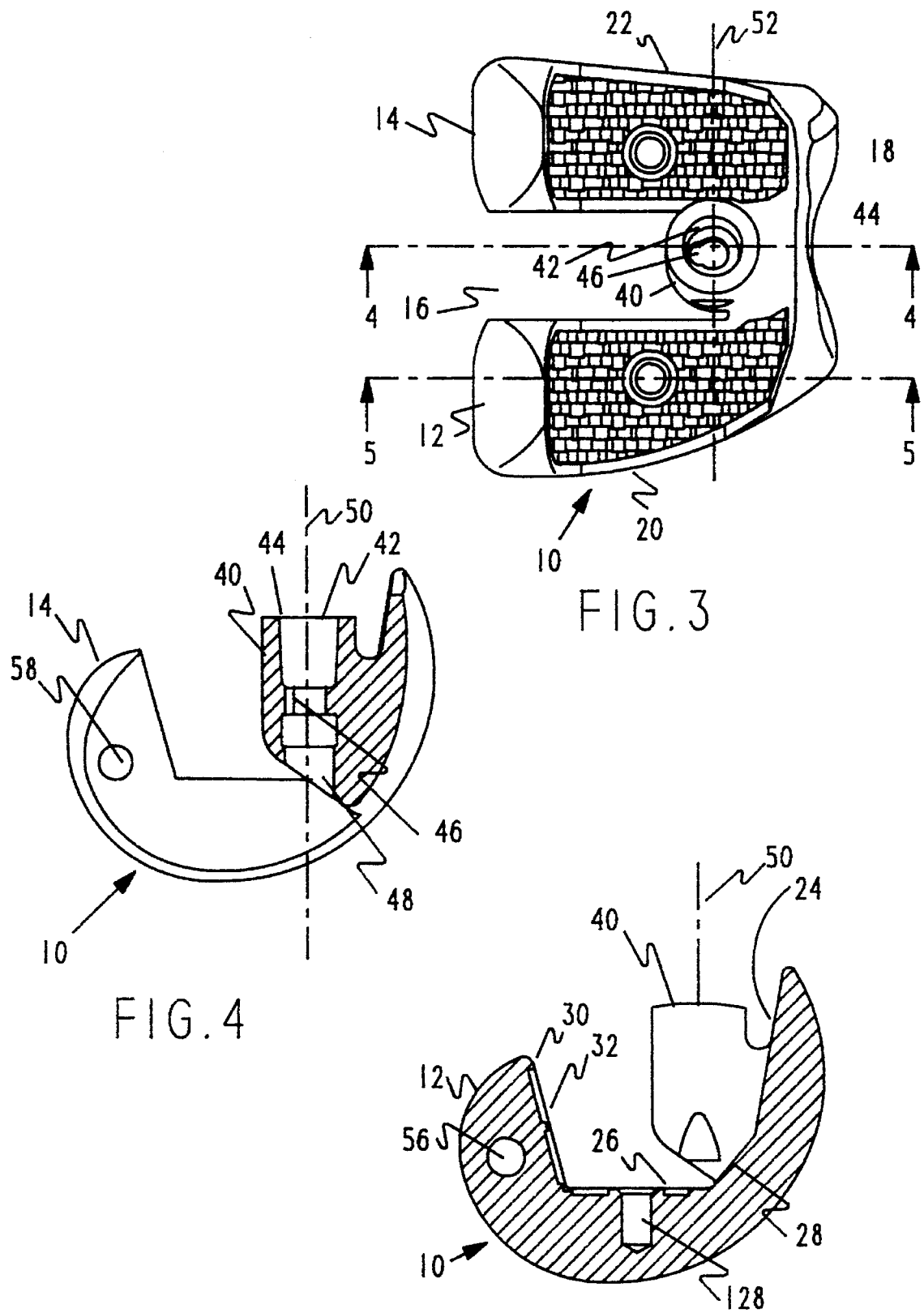

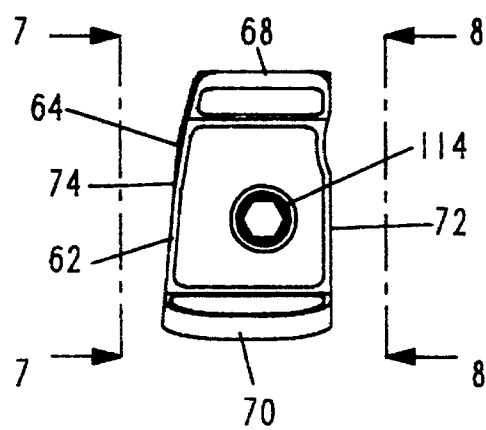
FIG. 6
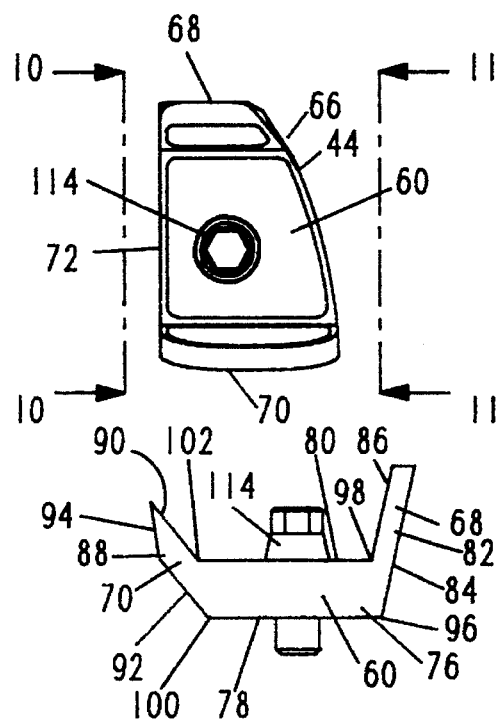
FIG. 9
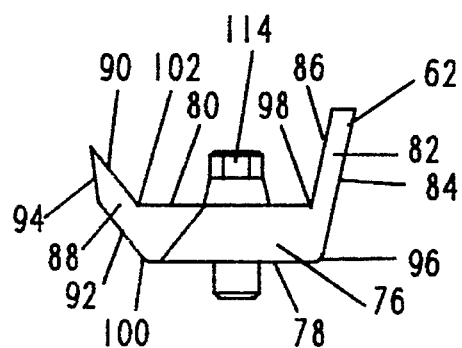
FIG. 7
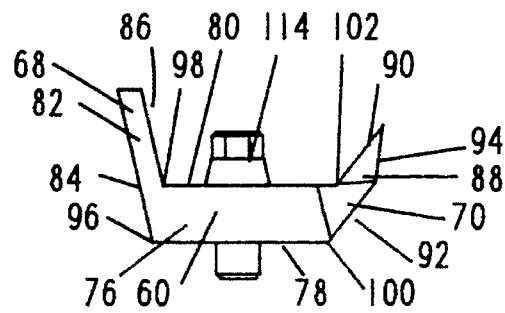
FIG. 10
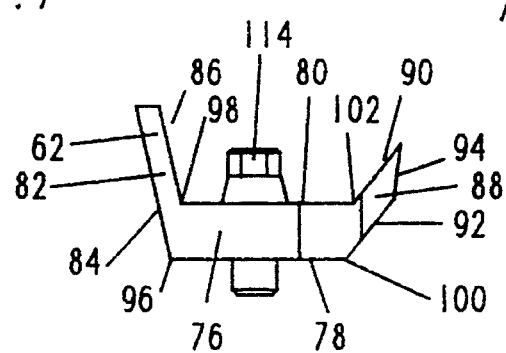
FIG. 8
FIG. 11

KNEE REVISION PROSTHESIS WITH SHIMS

This application is a continuation of co-pending application Ser. No. 08/331,049 filed on Oct. 28, 1994.

FIELD OF MY INVENTION

My invention relates to prosthetic joints generally and specifically to a knee prosthesis, particularly adapted for revision surgery, having femoral shims or spacers to accommodate loss of bone.

BACKGROUND OF MY INVENTION

Orthopedic implants for the human knee generally have a femoral and a tibial component. The tibial component is usually placed on the resected proximal surface of the tibia and frequently has a metal baseplate with a shaft extending into the tibial medullar canal. The baseplate usually carries an ultra high molecular weight polyethylene (UHMWPE) articulating surface. The articulating surface has a medial and lateral condyle compartment. A femoral component is implanted on a resected distal end of the femur and presents artificial condyles to articulate with the condyle compartments of the tibial component. A femoral component generally comprises the condyle articulating surfaces and fixation means which may include an elongated stem which extends into the femoral medullar canal of the patient. Such prosthesis are well-known and examples can be found in U.S. Pat. Nos. 4,963,152; 5,062,852; and 5,071,438.

For patients who require an artificial knee prosthesis, degeneration of the bone at either the tibia or femur or both may be occurring. Moreover, this degeneration may be proceeding unevenly with respect to the two condyles. It is also known that some patients require a reoperation and the installation of what is called a "revision" knee prosthesis. The revision knee prosthesis is generally more massive than a so-called "primary" knee prosthesis. The revision femoral knee condylar parts may be thicker and more robust and the medullar shaft may be substantially longer. Moreover, in many cases degeneration of one condyle may be substantially more advanced than the other.

In such cases, it is advantageous to be able to retain as much bone in each condyle as possible. This, however, may result in uneven resection of the condyles. One can compensate for this disparity by providing shims of varying thickness which can be placed on one condyle or the other or both to raise the surfaces in an appropriate fashion.

SUMMARY OF MY INVENTION

In a knee prosthesis of my invention, the femoral prosthesis has an internal geometry adjacent the femur which has four intersecting planes which extend from the medial side of the prosthesis to the lateral side. Using this geometry, shims of varying thickness can be added which retain the same internal box geometry. The internal geometry of the shims comprises three intersecting planes. Medial and lateral shims are provided. The internal geometry of the shims must be translated slightly anteriorly as they increase in thickness. The shims may be added to either condyle independently, with different thickness on each side.

With the foregoing in mind, it is the principal object of my invention to provide a femoral knee prosthesis which will maintain a common internal box geometry for installation of shims.

It is a further object of my invention to provide such a prosthesis with shims of independently selected thickness for each condyle.

These and other objects and features of my invention will be apparent from the following detailed description taken with respect to the accompanying drawings.

BRIEF DESCRIPTION OF THE DRAWINGS

FIG. 3 is a top view of the prosthesis of FIG. 1 without shims.

FIG. 4 is a partial through section of the prosthesis of FIG. 3, taken along line 4—4.

FIG. 5 is a partial through section of the prosthesis of FIG. 3 taken along line 5—5.

FIG. 6 is a top view of a lateral condyle shim for use in my invention.

FIG. 7 is an outside plan view of the shim of FIG. 6, taken on line 7—7 in FIG. 6.

FIG. 8 is a side plan view of the shim of FIG. 6, taken along line 8—8.

FIG. 9 is a top plan view of a medial condyle shim for use with my invention.

FIG. 10 is an inside plan view of the medial condyle shim of FIG. 9 taken along line 10—10.

FIG. 11 is an outside plan view of the medial condyle shim of FIG. 9 taken along line 11—11.

DETAILED DESCRIPTION OF MY PREFERRED EMBODIMENT

Figure 1:
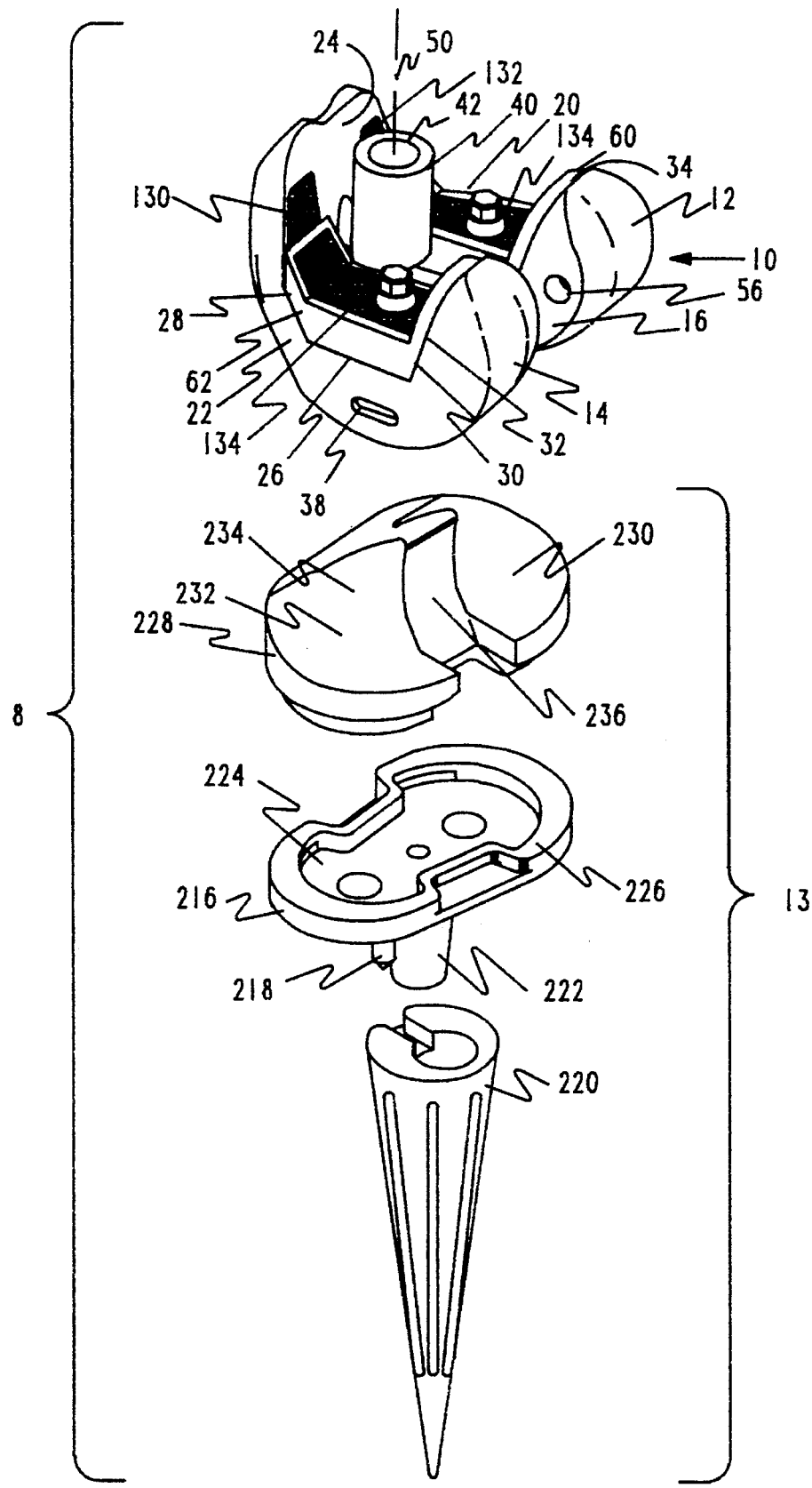
FIG. 1 is a perspective view of a revision knee prothesis with shims in accordance with my invention.

I will now describe my invention with respect to the accompanying drawings. Like numerals will refer to like parts throughout all the drawings. A revision prosthetic knee prosthesis 8 is illustrated in perspective view in FIG. 1. The femoral component is generally designated 10. The femoral component has a medial articulating surface 12 and a lateral articulating surface 14, which correspond to the anatomical condyles of a human femur. These articulating surfaces conventionally present polished surfaces which will slide against a low friction surface on a prosthetic tibial component 13. Posteriorly, the articulating surfaces 12, 14 are separated by a gap 16 as can be seen in FIG. 1. Anteriorly, the articulating surfaces 12, 14 are joined by a channel 18 wherein the patient's patella, or an artificial surface attached to the patella, will rest when the implant is complete. The femoral component 10 has an internal box geometry comprised of four intersecting planes which extend from a medial side 20 to a lateral side 22 of the component. These planes can be seen most effectively in FIG. 5. An anterior stabilizing plane 24 lies behind the channel 18 and will abut a resected surface on the anterior side of the patient's femur, when the component 10 is implanted. A base plane 26 will abut a distal end of the femur when the component is implanted and carries most of the load when a patient is walking or standing. Between the anterior plane and the base plane 26 there is a chamfer plane 28 which is provided so that the prosthetic component 10 does not become unduly thin at the junction of the anterior plane 24 and the base plane 26. Finally, a posterior plane 30 is opposed to the anterior plane 24. The posterior plane 30 will lie adjacent a resected surface on the posterior of the patient's femur when the component is implanted. The posterior plane 30 is divided into two parts by the gap 16, such that there is a lateral posterior surface 32 associated with the lateral, condyle articulating surface 14 and a medial posterior surface 34 associated with the medial condyle articulating surface 12.

The tibial component 13 comprises a base plate 216 with fixation means for attaching the base plate 216 to the resected upper surface of a tibia. In the illustrated embodiment, the fixation means comprise pins 218 and a removable shaft 220 for insertion into the medullary canal of the tibia. The shaft 220 is releasably mounted on a post 222. Other features, known in the art, may be provided, such as porous surfaces, or fixation screws. The base plate 216 has a superior cavity 224 surrounded by a lip 226 for receiving an insert 228 of ultra high molecular weight polyethylene. The insert 228 has medial and lateral articulating surfaces 230, 232 respectively. The articulating surfaces 230, 232 are separated by a central stabilizing eminence 234. If it is desirable to use the prosthesis without a posterior stabilizing feature, an insert without the stabilizing eminence would be employed, as is known in the art. This is simply a matter of substituting one insert for another. The stabilizing eminence 234 has a posterior surface 236 for engaging a pin in the femoral component.

Figure 13:
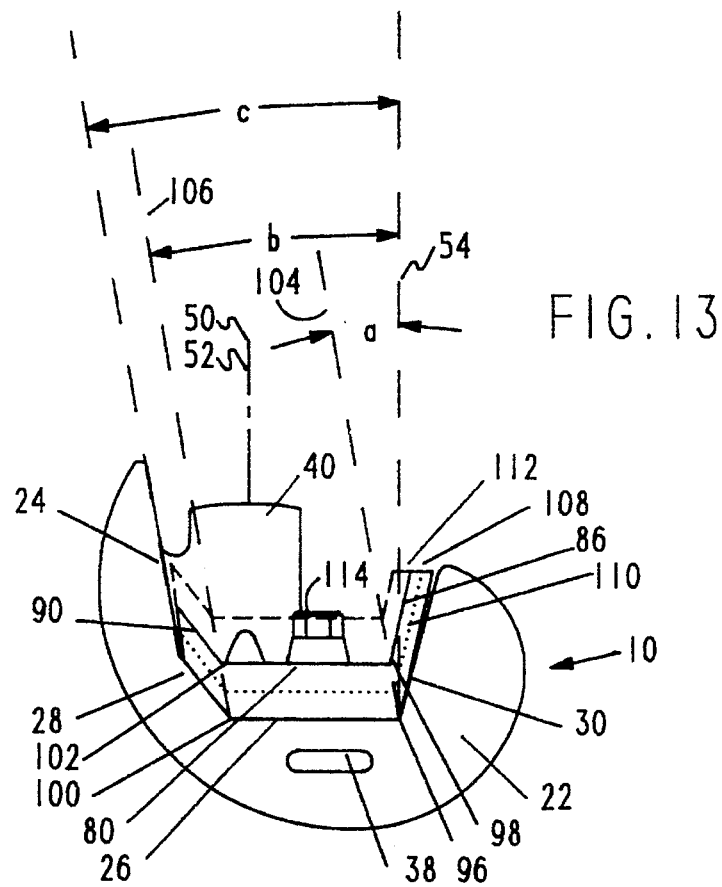
FIG. 13 is a side plan view of the femoral knee prosthesis of FIG. 1 illustrating the effect of shims of varying thickness.
Figure 12:
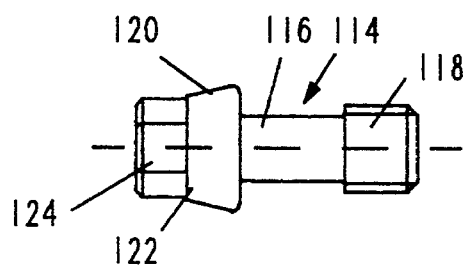
FIG. 12 is a plan view of a screw for use in fastening shims to the femoral knee prosthesis.

I anticipate that the femoral component and shim combination of my invention will find principle application in connection with revision knee prosthesis, that is, in connection with prosthesis where a substantial amount of distal femoral or proximal tibial bone must be removed. Consequently, the femoral component 10 is illustrated as a robust, massive component. To facilitate implantation or removal, a medial slot 36 on the medial side 20 of the component 10 and a lateral slot 38 on the lateral side 22 of the component 10 may be provided. Instruments may be inserted into these slots to provide a grip for a surgeon to remove or otherwise manipulate the component. Centrally within the interior box geometry a post 40 is provided. The post 40 has a central bore 42 for receiving a medullar shaft (not shown). It is known in the art of prosthetic knee design to provide shafts which extend into the medullar canal of a patient. Such shafts provide increased stability and fixation. In connection with a revision prosthesis, a particularly long shaft may be desired. Consequently, a modular design, where the length of the shaft may be selected for its length and affixed to the component intraoperatively, is my preferred embodiment. The bore 42 can comprise different means for securing the shaft. For example, a tapered segment 44 may provide a conical interlock, such as a morse taper. A slot 46 may be provided to inhibit rotation of the shaft. Finally, a distal chamber 48 could receive a nut on a threaded portion of the shaft. Additional securing means may be selected, as is known in the art. The post 40 and bore 42 define a medullar axis 50 which would extend along the medullar canal of the patient when the component was implanted. A medial-lateral plane 52 through the axis 50 defines a reference plane for further description of the internal box geometry of the component 10. The relationship of the planes 24, 26, 28 and 30 to the medial-lateral plane 52 and axis 50 can be seen most readily in FIG. 13. For clarity of explanation, I have illustrated a plane 54 parallel to, but offset posteriorly from the medial-lateral plane 52. As can be seen in FIG. 13, the anterior plane 24 of the component 10 forms an acute angle c with the plane 54. The same angle would, of course, be formed with the medial lateral plane 52. It can be seen that the posterior plane 30 also forms an acute angle with the plane 54. The anterior plane 24 and the posterior plane 30 converge distally. The base plane 26 is generally at right angles to the medial-lateral plane 52 and is orthogonal to the axis 50. The importance of this geometry will be explained hereafter in connection with the shims of my invention.

In addition to the features described heretofore, the femoral component 10 may also be provided with an optional transverse bar (not shown) between the posterior surfaces 32, 34 and extending across the gap 16. Such a bar is described by Hofmann in U.S. Pat. No. 5,116,375 and further in U.S. Pat. No. 5,405,398 assigned to Intermedics Orthopedics, Inc., the assignee of my invention. Such a bar may be optionally placed in a femoral component to convert the component to a posterior stabilized configuration. Posterior stabilized femoral components, and associated tibial components are known in the art and are particularly useful when the patient's posterior cruciate ligaments have been removed, as may frequently be the case in connection with revision surgery. To receive such a bar, a transverse through bore 56 and a transverse stopped bore 58 are provided in the medial posterior surface 34 and the lateral posterior surface 32 respectively. Further information on the transverse bar for posterior stabilization may be had from Hofmann U.S. Pat. No. 5,116,375 patent and U.S. Pat. No. 5,405,398 which are incorporated herein by reference.

My invention provides for a set of shims which may be selectively attached in the interior box of the femoral component 10. As illustrated in FIG. 1, a medial shim 60 and a lateral shim 62 are preferably provided, although a single shim extending across the entire component 10 could also be used. The thickness of the medial and lateral shims 60, 62 are selected independently from each other. Moreover, a medial shim may be used without a lateral shim, or a lateral shim may be used without a medial shim. As seen in FIG. 6 and FIG. 9, the lateral shim 62 and the medial shim 60 have a general peripheral outline 64, 66, respectively, associated with the design of the femoral component 10 as can be seen in FIG. 3. In general, each shim has a front side 68, a rear side 70, an inner side 72 adjacent the post 40, and an outer side 74 spaced away from the post 40. On the lateral shim, 62, the outer side 74 conforms to the lateral side 22 of the component 10. On the medial shim 60 the outer side 74 conforms to the medial side 20 of the component 10.

Each shim has a base portion 76 which, when assembled, lies adjacent the base plane 26. The base portion 76 is defined by a bottom 78 and a top 80 which are spaced apart from, but parallel to each other. Each shim also has a posterior portion 82 which, when assembled, lies adjacent the posterior plane 30. The posterior portion 82 is defined by a rear wall 84 and a front wall 86. The walls 84, 86 are parallel to each other, but spaced apart from one another. Finally, each shim has a chamfer portion 88. The chamfer portion 88 lies adjacent the chamfer plane 28 when assembled. There is no portion which extends solely along the anterior plane 24. The chamfer portion 88 is defined by an upper wall 90 and a lower wall 92. The lower wall 92 faces the chamfer plane 28 in the assembled condition. The upper wall 90 and the lower wall 92 are spaced apart from, but parallel to each other. The chamfer portion 88 is also defined by an anterior wall 94 which lies adjacent the anterior plane 24 when assembled.

The junction of the back wall 84 and the bottom 78 form a first corner 96. The junction of the front wall 86 and the top 80 form a second corner 98. The junction of the lower wall 92 and the bottom 78 form a third corner 100, and the junction of the upper wall 90 and the top 80 form a fourth corner 102. A plane established through the first corner 96 and the second corner 98 (shown as line 104 in FIG. 13) would be parallel to the anterior plane 24 and would form an angle a with the plane 54 as shown in FIG. 13. Similarly, a plane established between the third corner 100 and the fourth corner 102, (indicated by line 106 in FIG. 13) would also be parallel to the anterior plane 24 and would form an angle b with the plane 54. The angles a, b and c are non-zero and equal. In my preferred embodiment, the angles a, b and c are between 5 and 15 degrees and most preferably 10 degrees.

Figure 14:
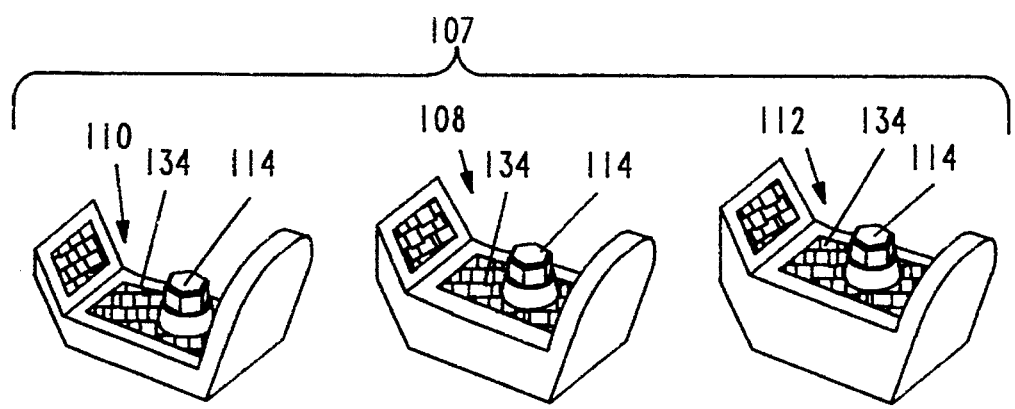
FIG. 14 illustrates a set of shims of varying thickness.

The effect of my invention can be seen most readily in FIG. 13. A first shim 108 is shown in solid outline. The first shim 108 has a thickness selected to correspond to the needs of the particular patient with whom the component 10 is being used. Note that the internal geometry, comprised of the anterior plane 24, the upper wall 90, the top 80 and the front wall 86, is congruent with the internal geometry of the component 10 comprised of the anterior plane 24, the chamfer plane 28, the bottom plane 26 and the posterior plane 30, but is translated anteriorly along the anterior plane 24. A thinner, second shim 110 is shown in dotted outline and a thicker, third shim 112 is shown in dashed outline. The set 107 of three shims 108, 110 and 112 can also be seen in perspective view in FIG. 14.

By shifting the second and fourth corners, 98 and 102 respectively, parallel to the anterior plane 24, it is possible to maintain this constant internal geometry. At the same time, the posterior portion 82 of the shim stays relatively thick, so that its structural integrity may be maintained. If a portion of the shim were used along both the anterior plane 24 and the posterior plane 30, the two portions of the shim, particularly for thin shims, might become so thin as to be deformable or at least flexible, which would not be a desirable condition.

It will be apparent that if different thicknesses of shim are used on the medial and lateral sides of the component 10, that the resections for each condyle must be different. Such resections are most advantageously made in connection with a specialized jig, such as the jig designed for use with my invention by Charles Mumme, which has been assigned to our common assignee, Intermedics Orthopedics, Inc. and which is disclosed in U.S. Pat. No. 5,411,505, the disclosure of which is incorporated herein.

Figure 2:
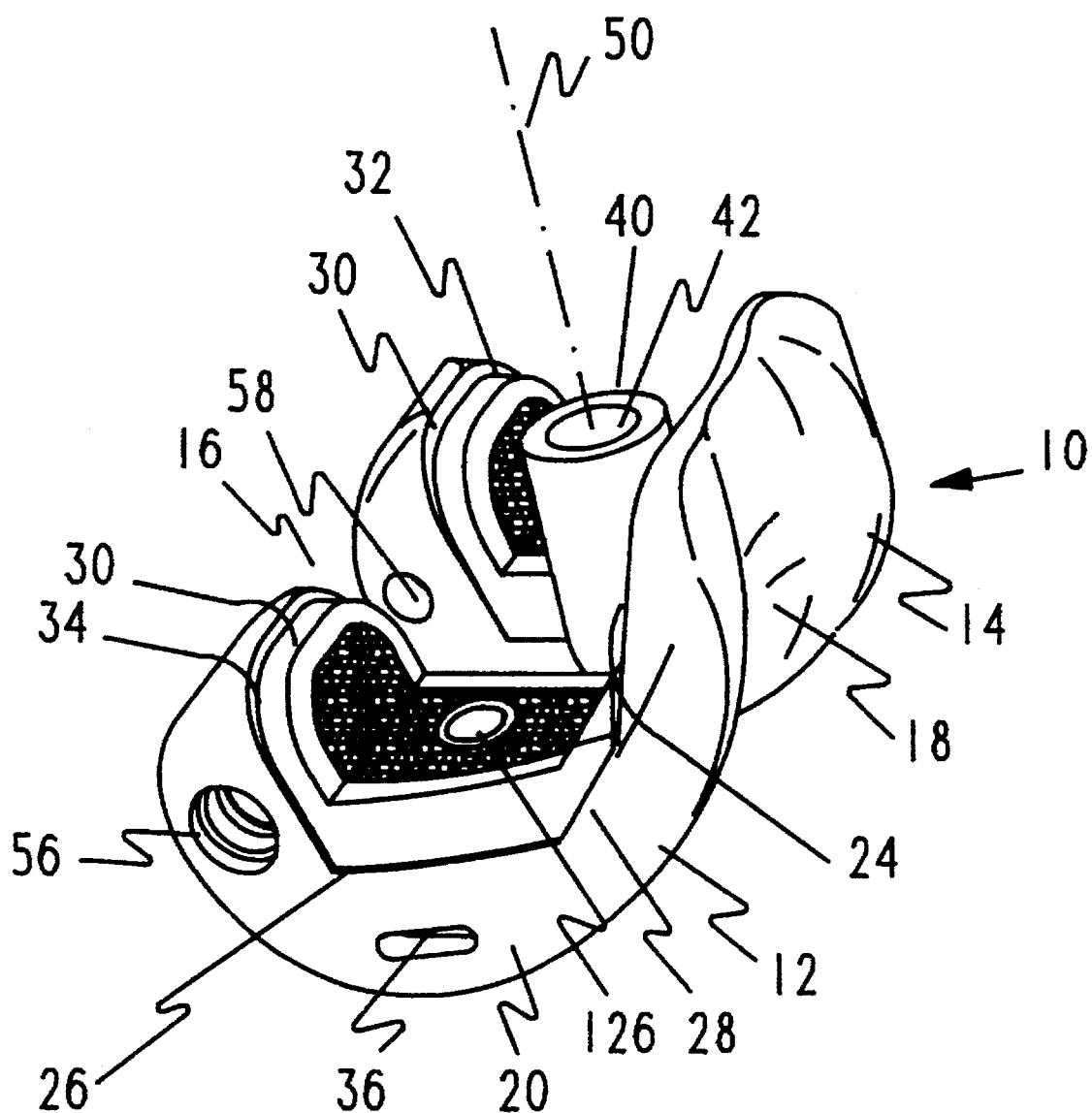
FIG. 2 is a second perspective view of the prosthesis and shims of FIG. 1.

The shims of my invention are attached to the femoral component 10, preferably by a screw 114. The screw 114 serves the dual function of attaching a shim and providing a stabilizing feature by being inserted into the distal portion of the patient's femur. The screw 114 comprises a shank 116 with a threaded end 118 and a head 120. The head 120 comprises a frustro-conical segment 122 and a hexagonal portion 124. Each of the shims is provided with a central threaded bore 126, as shown in FIG. 2. The threaded portion 118 of the screw 114 is threaded through the threaded bore 126 so that the screw 114 is essentially captured in the shim. The assembly of the shim and screw can then be attached to the component 10 by threading the screw into a threaded stopped bore, such as bore 128 shown in FIG. 5. In addition a surgeon may chose to put bone cement between the component 10 and a spacer 62.

Additional features may also be used with my invention. For example, porous areas, such as areas 130 and 132 on the femoral component 10, may be provided for ingrowth of bone, as is known in the art. Similarly, the shims may have areas of porous coating 134 where ingrowth of bone may occur. The use of porous and textured coatings to encourage affixation of a prothesis to bone is well known in the art and need not be further described here.

The use of my invention will maintain the same congruent internal box geometry for each condyle, while providing shims which are independently selectable, and do not have unduly thin portions. The use of this system permits the surgeon the retain as much of the patient's bone as possible while compensating for the degeneration for the bone on either the medial or lateral condyle, depending on circumstances.

My invention may be embodied in other specific forms without departing from the teachings thereof. The foregoing description, therefore, is to be consider in all respects to be illustrative and not restrictive. The scope of my invention is defined by the following claims, and all changes within the scope of equivalency of the claims are intended to be encompassed therein.

I claim as my invention:

1. An implantable knee prosthesis comprising:

a tibial component having medial and lateral articulating surfaces;

a femoral component having medial and lateral condylar articulating surfaces configured to engage and articulate against said medial and lateral articulating surfaces, respectively, of said tibial component, said femoral component having planar surfaces configured to engage resected bone surfaces on a distal end of a femur and arranged relative to an axis to define an internal box geometry, including:

a base planar surface forming a substantially right angle with said axis and having a length in an anterior-posterior direction, an anterior planar surface forming an acute angle with said axis, a posterior planar surface intersecting said base planar surface at a first corner, said posterior planar surface being spaced from and disposed substantially in opposition to said anterior planar surface, and a chamfer planar surface intersecting said anterior planar surface, and intersecting said base planar surface at a third corner, and having a length in an anterior-posterior direction; and a shim including a base portion, a posterior portion, and a chamfer portion;

said base portion including a bottom wall lying adjacent said base planar surface, and a top wall spaced from and substantially parallel to said bottom wall, said top wall having a length in an anterior-posterior direction, which length is substantially equal to said length of said base planar surface;

said posterior portion including a rear wall lying adjacent said posterior planar surface, and a front wall spaced from and substantially parallel to said rear wall, said front wall intersecting said top wall at a second corner;

said chamfer portion including a lower wall lying adjacent said chamfer planar surface, and an upper wall spaced from and substantially parallel to said lower wall, said upper wall intersecting said top wall at a fourth corner and having a length in an anterior-posterior direction which length is substantially equal to said length of said chamfer planar surface;

wherein said second corner is displaced from said first corner in a direction substantially parallel to said anterior plane, and said fourth corner is displaced from said third corner in a direction substantially parallel to said anterior plane, such that said top wall, front wall and upper wall of said shim, together with said anterior planar surface of said femoral component, define an internal box geometry that is congruent with but displaced from said internal box geometry defined by said planar surfaces of said femoral component.

2. The prosthesis of claim 1 wherein said acute angle is between about 5 degrees and about 15 degrees.

3. The prosthesis of claim 2 wherein said acute angle is between about 9 degrees and about 11 degrees.

4. The prosthesis of claim 3 wherein said acute angle is about 10 degrees.

5. The prosthesis of claim 1 wherein said shim comprises a medial shim and a lateral shim.

6. The prosthesis of claim 1, and further including a screw securing said shim to said femoral component.

7. The prosthesis of claim 6 wherein said shim has a threaded bore for receiving said screw and wherein said screw has a head, a threaded portion and a shank between said head and said threaded portion, said shank being adapted to be loosely received within said threaded bore, whereby said screw is captured in said shim.

8. The prosthesis of claim 7 wherein said head of said screw further comprises means for enhancing fixation of said femoral component to said femur.

9. The prothesis of claim 1 in which said shim further includes an anterior wall lying adjacent said anterior planer surface of said femoral component and intersecting said lower wall and said upper wall.

10. An implantable knee prosthesis kit comprising:
a tibial component having medial and lateral articulating surfaces;
a femoral component having medial and lateral condylar articulating surfaces configured to engage and articulate against said medial and lateral articulating surfaces, respectively, of said tibial component, said femoral component having planar surfaces configured to engage resected bone surfaces on a distal end of a femur and arranged relative to an axis to define an internal box geometry, including:
a base planar surface forming a substantially right angle with said axis and having a length in an anterior-posterior direction,
an anterior planar surface forming an acute angle with said axis,
a posterior planar surface intersecting said base planar surface at a first corner, said posterior planar surface being spaced from and disposed substantially in opposition to said anterior planar surface, and
a chamfer planar surface intersecting said anterior planar surface, and intersecting said base planar surface at a third corner and having a length in an anterior-posterior direction; and
a plurality of interchangeable shims of different thicknesses, any one of which can be selected for use with said femoral component, any such selected shim including a base portion, a posterior portion, and a chamfer portion;
said base portion including a bottom wall lying adjacent said base planar surface, and a top wall spaced from and substantially parallel to said bottom wall and having a length in an anterior-posterior direction which length is substantially equal to said length of said base planar surface;
said posterior portion including a rear wall lying adjacent said posterior planar surface, and a front wall spaced from and substantially parallel to said rear wall, said front wall intersecting said top wall at a second corner;
said chamfer portion including a lower wall lying adjacent said chamfer planar surface, and an upper wall spaced from and substantially parallel to said lower wall, said upper wall intersecting said top wall at a fourth corner and having a length in an anterior-posterior direction which length is substantially equal to said length of said chamfer planar surface;
wherein said second corner is displaced from said first corner in a direction substantially parallel to said anterior plane, and said fourth corner is displaced from said third corner in a direction substantially parallel to said anterior plane, such that said top wall, front wall and upper wall of said shim, together with said anterior planar surface of said femoral component, define an internal box geometry that is congruent with but displaced from said internal box geometry defined by said planar surfaces of said femoral component.

11. The knee prosthesis kit of claim 10 wherein said acute angle is between about 5 degrees and about 15 degrees.

12. The knee prosthesis kit of claim 11 wherein said acute angle is between about 9 degrees and about 11 degrees.

13. The knee prosthesis kit of claim 12 wherein said acute angle is about 10 degrees.

14. The knee prosthesis kit of claim 13 wherein said shim comprises a medial shim and a lateral shim.

15. The knee prosthesis kit of claim 13, and further including a screw securing said shim to said femoral component.

16. The knee prosthesis kit of claim 15 wherein said shim has a threaded bore for receiving said screw and wherein said screw has a head, a threaded portion and a shank between said head and said threaded portion, said shank being adapted to be loosely received within said threaded bore, whereby said screw is captured in said shim.

17. The knee prosthesis kit of claim 16 wherein said head of said screw further comprises means for enhancing fixation of said femoral component to said femur.

18. The knee prothesis kit of claim 10 in which said shim further includes an anterior wall lying adjacent said anterior planer surface of said femoral component and intersecting said lower wall and said upper wall.

* * * * *